United States Patent
Fang et al.

(10) Patent No.: US 9,222,046 B2
(45) Date of Patent: Dec. 29, 2015

(54) ALKOXYLATED QUATERNARY AMMONIUM SALTS AND DIESEL FUELS CONTAINING THE SALTS

(71) Applicant: Afton Chemical Coporation, Richmond, VA (US)

(72) Inventors: Xinggao Fang, Midlothian, VA (US); Scott D. Schwab, Richmond, VA (US)

(73) Assignee: Afton Chemical Corporation, Richmond, VA (US)

( * ) Notice: Subject to any disclaimer, the term of this patent is extended or adjusted under 35 U.S.C. 154(b) by 247 days.

(21) Appl. No.: 13/871,508

(22) Filed: Apr. 26, 2013

(65) Prior Publication Data

US 2014/0318487 A1    Oct. 30, 2014

(51) Int. Cl.
| | | |
|---|---|---|
| C10L 1/222 | (2006.01) | |
| C10L 1/188 | (2006.01) | |
| C10L 1/224 | (2006.01) | |
| C10L 10/18 | (2006.01) | |
| C10L 1/183 | (2006.01) | |
| C10L 10/06 | (2006.01) | |
| C07C 233/38 | (2006.01) | |

(52) U.S. Cl.
CPC ............. *C10L 1/1881* (2013.01); *C07C 233/38* (2013.01); *C10L 1/1832* (2013.01); *C10L 1/224* (2013.01); *C10L 10/06* (2013.01); *C10L 10/18* (2013.01); *C10L 2200/029* (2013.01); *C10L 2200/0446* (2013.01); *C10L 2270/026* (2013.01)

(58) Field of Classification Search
CPC .................... C10L 1/2222; C10L 2270/026
USPC ......................................................... 44/422
See application file for complete search history.

(56) References Cited

U.S. PATENT DOCUMENTS

| | | | |
|---|---|---|---|
| 2,589,674 A | 3/1952 | Cook et al. | |
| 4,338,206 A | 7/1982 | Hammond et al. | |
| 4,482,357 A | 11/1984 | Hanlon | |
| 4,621,141 A | 11/1986 | Chibnik | |
| 4,631,071 A | 12/1986 | Axelrod et al. | |
| 4,657,562 A | 4/1987 | Axelrod et al. | |
| 6,964,940 B1 | 11/2005 | Treybig et al. | |
| 7,518,005 B2 * | 4/2009 | Patil et al. | 554/52 |
| 7,947,093 B2 | 5/2011 | Barton et al. | |
| 7,951,211 B2 | 5/2011 | Barton et al. | |
| 8,147,569 B2 | 4/2012 | Barton et al. | |
| 8,690,970 B2 * | 4/2014 | Fang | 44/422 |
| 8,915,977 B2 * | 12/2014 | Fang et al. | 44/422 |
| 8,961,623 B2 * | 2/2015 | Stevenson et al. | 44/422 |
| 8,992,636 B1 * | 3/2015 | Fang et al. | 44/419 |
| 2006/0182696 A1 | 8/2006 | Patil et al. | |
| 2008/0113890 A1 | 5/2008 | Moreton et al. | |
| 2011/0258917 A1 | 10/2011 | Garcia Castro et al. | |
| 2012/0010112 A1 | 1/2012 | Grabarse et al. | |
| 2012/0138004 A1 | 6/2012 | Stevenson et al. | |
| 2013/0031827 A1 | 2/2013 | Reid et al. | |
| 2013/0031828 A1 | 2/2013 | Reid et al. | |
| 2013/0104826 A1 | 5/2013 | Burgess et al. | |
| 2013/0233267 A1 | 9/2013 | Barbour | |
| 2014/0345191 A1 * | 11/2014 | Bush et al. | 44/347 |
| 2015/0072910 A1 * | 3/2015 | Moreton et al. | 508/389 |
| 2015/0096528 A1 * | 4/2015 | Schwab et al. | 123/294 |

FOREIGN PATENT DOCUMENTS

| | | | |
|---|---|---|---|
| EP | 0343981 A1 | 11/1989 | |
| WO | 2011149799 A1 | 12/2011 | |
| WO | 2011161149 A1 | 12/2011 | |

* cited by examiner

*Primary Examiner* — Ellen McAvoy
(74) *Attorney, Agent, or Firm* — Luedeka Neely Group, P.C.

(57) ABSTRACT

A fuel soluble additive for a diesel engine, a method for improving performance of fuel injectors and a method for cleaning fuel injectors for a diesel engine. The fuel soluble additive includes a quaternary ammonium salt derived from an amido amine containing at least one tertiary amino group and an epoxide, in the presence of a proton donor selected from a carboxylic acid and an alkyl phenol. The amido amine is made in a reaction medium that is substantially devoid of an acylating agent.

13 Claims, No Drawings

ALKOXYLATED QUATERNARY AMMONIUM SALTS AND DIESEL FUELS CONTAINING THE SALTS

TECHNICAL FIELD

The disclosure is directed to a diesel fuel additive and to diesel fuels that include the additive that are useful for improving the performance of direct fuel injected engines. In particular the disclosure is directed to an alkoxylated quaternary ammonium salt fuel additive that is effective to enhance the performance of direct fuel injectors for diesel engines.

BACKGROUND AND SUMMARY

It has long been desired to maximize fuel economy, power and driveability in diesel fuel powered vehicles while enhancing acceleration, reducing emissions, and preventing hesitation. While it is known to enhance gasoline powered engine performance by employing dispersants to keep valves and fuel injectors clean in port fuel injection engines, such gasoline dispersants are not necessarily effective direct fuel injected diesel engines. In addition, dispersants for indirect fuel injected diesel engines may not be effective for direct fuel injected diesel engines. The reasons for this unpredictability lie in the many differences between the direct and indirect fuel injected diesel engines and the fuels suitable for such engines.

For example, there is a dramatic difference between indirect fuel injected diesel engines, and more modern high pressure common rail (HPCR), direct fuel injected diesel engines. Also, low sulfur diesel fuels and ultra low sulfur diesel fuels are now common in the marketplace for such engines. A "low sulfur" diesel fuel means a fuel having a sulfur content of 50 ppm by weight or less based on a total weight of the fuel. An "ultra low sulfur" diesel fuel (ULSD) means a fuel having a sulfur content of 15 ppm by weight or less based on a total weight of the fuel. Fuel injectors in an HPCR engine perform at much higher pressures and temperatures compared to older style engines and fuel injection systems. The combination of low sulfur or ULSD and HPCR engines have resulted in a change to the type of injector deposits and frequency of formation of injector deposits now being found in the marketplace.

Over the years, dispersant compositions for diesel fuels have been developed. Dispersant compositions known in the art for use in fuels include compositions that may include polyalkylene succinimides, polyamines and polyalkyl substituted Mannich compounds. Dispersants are suitable for keeping soot and sludge suspended in a fluid, however the foregoing dispersants are not particularly effective for cleaning surfaces once deposits have formed on the surfaces.

Hence, fuel compositions for direct fuel injected diesel engines often produce undesirable deposits in the internal engine surfaces and fuel filters. Accordingly, improved compositions that can prevent deposit build up, maintaining "as new" cleanliness for the vehicle life are desired. Ideally, the same composition that can clean up dirty fuel injectors restoring performance to the previous "as new" condition would be equally desirable and valuable in the attempt to reduce air borne exhaust emissions and to improve the power performance of the engines.

In accordance with the disclosure, exemplary embodiments provide a fuel soluble additive for a diesel engine, a diesel fuel containing the additive, a method for improving performance of fuel injectors and a method for cleaning fuel injectors for a diesel engine. The fuel soluble additive includes a quaternary ammonium salt derived from an amido amine containing at least one tertiary amino group and an epoxide, in the presence of a proton donor. The amido amine is made in a reaction medium that is substantially devoid of an acylating agent.

Another embodiment of the disclosure provides a method of improving the injector performance of a direct fuel injected diesel engine. The method includes operating the engine on a diesel fuel composition containing a major amount of diesel fuel and from about 5 to about 100 ppm by weight based on a total weight of the fuel composition of a quaternary ammonium salt derived from an amido amine containing at least one tertiary amino group and an epoxide, in the presence of a proton donor selected from a carboxylic acid and an alkyl phenol. The amido amine is made in a reaction medium that is substantially devoid of an acylating agent.

A further embodiment of the disclosure provides a method of operating a direct fuel injected diesel engine. The method includes combusting in the engine a fuel composition containing a major amount of fuel and from about 5 to about 100 ppm by weight based on a total weight of the fuel composition of a quaternary ammonium salt derived from an amido amine containing at least one tertiary amino group and an epoxide, in the presence of a proton donor selected from a carboxylic acid and an alkyl phenol. The amido amine is made in a reaction medium that is substantially devoid of an acylating agent.

In another embodiment of the fuel additive, an amido amine is derived from a fatty acid.

An advantage of the fuel additive described herein is that the additive may not only reduce the amount of deposits forming on fuel injectors, but the additive may also be effective to clean up dirty fuel injectors sufficient to provide improved power recovery to the engine.

Another advantage of the fuel additive described herein is that it may be used at a much lower concentration than a quaternary ammonium salt derived made from an amine that is derived from an acylating agent, yet provide better injector cleanliness performance than conventional quaternary ammonium salts made from amines derived from acylating agents.

Additional embodiments and advantages of the disclosure will be set forth in part in the detailed description which follows, and/or can be learned by practice of the disclosure. It is to be understood that both the foregoing general description and the following detailed description are exemplary and explanatory only and are not restrictive of the disclosure, as claimed.

DETAILED DESCRIPTION OF EXEMPLARY EMBODIMENTS

The fuel additive component of the present application may be used in a minor amount in a major amount of fuel and may be added to the fuel directly or added as a component of an additive concentrate to the fuel. A particularly suitable fuel additive component for improving the operation of internal combustion engines may be made by reacting a tertiary amine of the formula

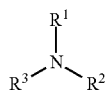

wherein each of $R^1$, $R^2$, and $R^3$ is selected from hydrocarbyl groups containing from 1 to 50 carbon atoms, with a carboxylic acid containing from 1 to 54 carbon atoms and a quaternizing agent to provide an alkoxylated quaternary ammonium salt. The reaction may be conducted in the presence of a protonating agent having an acid disassociation constant ($pK_a$) of less than about 13, such as a carboxylic acid or an alkyl phenol. The alkoxylated quaternary ammonium salt may also be derived from an amido amine and a quaternizing agent in the presence of a protonating agent. The protonating agent may be obtained from a carboxylic acid, alkyl phenol or from the amido amine derived from a fatty acid wherein the reaction product containing the amido amine has an acid number ranging from about 1 to about 200 mg KOH/g. Regardless of how the alkoxylated quaternary ammonium salt is made, a key feature of the disclosure is that the amine contains at least one tertiary amino group and the amido amine is made in a reaction medium that is substantially devoid of an acylating agent.

As used herein, the term "hydrocarbyl group" or "hydrocarbyl" is used in its ordinary sense, which is well-known to those skilled in the art. Specifically, it refers to a group having a carbon atom directly attached to the remainder of a molecule and having a predominantly hydrocarbon character. Examples of hydrocarbyl groups include:
(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);
(2) substituted hydrocarbon substituents, that is, substituents containing non-hydrocarbon groups which, in the context of the description herein, do not alter the predominantly hydrocarbon substituent (e.g., halo (especially chloro and fluoro), hydroxy, alkoxy, mercapto, alkylmercapto, nitro, nitroso, amino, alkylamino, and sulfoxy);
(3) hetero-substituents, that is, substituents which, while having a predominantly hydrocarbon character, in the context of this description, contain other than carbon in a ring or chain otherwise composed of carbon atoms. Hetero-atoms include sulfur, oxygen, nitrogen, and encompass substituents such as pyridyl, furyl, thienyl, and imidazolyl. In general, no more than two, or as a further example, no more than one, non-hydrocarbon substituent will be present for every ten carbon atoms in the hydrocarbyl group; in some embodiments, there will be no non-hydrocarbon substituent in the hydrocarbyl group.

As used herein, the term "major amount" is understood to mean an amount greater than or equal to 50 wt. %, for example from about 80 to about 98 wt. % relative to the total weight of the composition. Moreover, as used herein, the term "minor amount" is understood to mean an amount less than 50 wt. % relative to the total weight of the composition.

As used herein the term "substantially devoid of an acylating agent" means that the reaction product is made in the absence or substantial absence of a reaction product of a long chain hydrocarbon, generally a polyolefin substituted with a monounsaturated carboxylic acid reactant such as (i) α,β-monounsaturated $C_4$ to $C_{10}$ dicarboxylic acid such as fumaric acid, itaconic acid, maleic acid; (ii) derivatives of (i) such as anhydrides or $C_1$ to $C_5$ alcohol derived mono- or di-esters of (i); (iii) α,β-monounsaturated $C_3$ to $C_{10}$ monocarboxylic acid such as acrylic acid and methacrylic acid; or (iv) derivatives of (iii) such as $C_1$ to $C_5$ alcohol derived esters of (iii) with any compound containing an olefinic bond represented by the general formula:

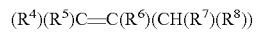

wherein each of $R^4$ and $R^5$ is, independently, hydrogen or a hydrocarbon based group. Each of $R^6$, $R^7$ and $R^8$ is, independently, hydrogen or a hydrocarbon based group; preferably at least one is a hydrocarbon based group containing at least 20 carbon atoms. Thus quaternized ammonium derivatives of acylating agents, such as described in U.S. Pat. Nos. 7,947,0931; 7,951,211; and 8,147,569 are shown herein to be less effective in power recovery than the recovery attained by the additives described herein.

Amine Compound

In one embodiment, a tertiary amine including diamines and polyamines may be reacted with a $C_1$ to $C_{54}$ carboxylic acid to form an amido amine and the amido amine may be subsequently reacted with a quaternizing agent. Suitable tertiary amido amine compounds of the formula

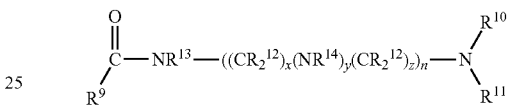

may be used, wherein each of $R^{10}$, and $R^{11}$ is selected from hydrocarbyl groups containing from 1 to 50 carbon atoms, each $R^9$, $R^{12}$, $R^{13}$ and $R^{14}$ may be independently selected from hydrogen or a hydrocarbyl group, x may range from 1 to 6, y may be 0 or 1, z may be 1 to 6, and n may range from 1 to 6. Each hydrocarbyl group $R^9$ to $R^{14}$ may independently be linear, branched, substituted, cyclic, saturated, unsaturated, or contain one or more hetero atoms. Suitable hydrocarbyl groups may include, but are not limited to alkyl groups, aryl groups, alkylaryl groups, arylalkyl groups, alkoxy groups, aryloxy groups, amino groups, and the like. Particularly suitable hydrocarbyl groups may be linear or branched alkyl groups. A representative example of an amine reactant which may be amidized and quaternized to yield compounds disclosed herein include for example, but are not limited to, dimethyl amino propyl amine.

If the amine contains solely primary or secondary amino groups, it may be desirable to alkylate at least one of the primary or secondary amino groups to a tertiary amino group prior to quaternizing the amido amine. In one embodiment, alkylation of primary amines and secondary amines or mixtures with tertiary amines may be exhaustively or partially alkylated to a tertiary amine and further alkoxylated to a quaternary salt.

Carboxylic Acid

When the amine has a primary or secondary amine group, the amine may be converted to an amido amine by reacting the amine with a $C_1$ to $C_{54}$ carboxylic acid. The acid may be a monoacid, a dimer acid, or a trimer acid. The acid may be selected from the group consisting of formic acid, acetic acid, propionic acid, butyric acid, caprylic acid, capric acid, lauric acid, myristic acid, palmitic acid, stearic, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and the dimer and trimer acids thereof. When reacted with the amine, the reaction product may be a $C_1$-$C_{54}$-alkyl or alkenyl-substituted amido amine such as a $C_1$-$C_{54}$-alkyl or alkenyl-substituted amido propyldimethylamine.

Quaternizing Agent

A suitable quaternizing agents may be selected from the group consisting hydrocarbyl epoxides of the formula:

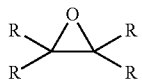

wherein each R is independently selected from H and a $C_1$ to $C_{50}$ hydrocarbyl group, and polyepoxides. Non-limiting examples of suitable epoxides that may be used as quaternizing agents may be selected from the group consisting of:
1,3-Butadiene diepoxide
Cyclohexene oxide
Cyclopentene oxide
Dicyclopentadiene dioxide
1,2,5,6-Diepoxycyclooctane
1,2,7,8-Diepoxyoctane
1,2-Epoxybutane
cis-2,3-Epoxybutane
3,4-Epoxy-1-butene
3,4-Epoxycyclohexylmethyl 3,4-epoxycyclohexanecarboxylate
1,2-Epoxydodecane
1,2-Epoxyhexadecane
1,2-Epoxyhexane
1,2-Epoxy-5-hexene
1,2-Epoxy-2-methylpropane
exo-2,3-Epoxynorbornane
1,2-Epoxyoctane
1,2-Epoxypentane
1,2-Epoxy-3-phenoxypropane
(2,3-Epoxypropyl)benzene
N-(2,3-Epoxypropyl)phthalimide
1,2-Epoxytetradecane
exo-3,6-Epoxy-1,2,3,6-tetrahydrophthalic anhydride
3,4-Epoxytetrahydrothiophene-1,1-dioxide
Isophorone oxide
Methyl-1,2-cyclopentene oxide
2-Methyl-2-vinyloxirane
α-Pinene oxide
Ethylene oxide
(±)-propylene oxide
Polyisobutene oxide
cis-Stilbene oxide
Styrene oxide
Tetracyanoethylene oxide
Tris(2,3-epoxypropyl) isocyanurate and combinations of two or more of the foregoing.

The quaternary ammonium salts from amido amines may be made in one stage or two stages. The reaction may be carried out by contacting and mixing the amido amine with the olefin oxide in the reaction vessel wherein a carboxylic acid is added to the reaction mixture to provide a protonating agent. The carboxylic acid may be same acid used to make the amido amine or may be selected from any of the above listed fatty acids, formic acid, acetic acid, propionic acid, butyric acid, polymeric acid and mixtures thereof, such a polyolefinic mono- or di-carboxylic acid, polymeric polyacids and mixtures thereof, and the like. When used, the mole ratio of protonating agent per mole of epoxy equivalents added to the reaction mixture may range from about 0.5:10, for example from about 2:5, or from abut 1:2 to about 2:1 moles of acid per mole of epoxy equivalents. In one embodiment, the anion of the quaternary ammonium salt is a carboxylate anion.

The reaction may be carried out at temperature ranging from about 30° to about 90° C., for example from about 45° to about 70° C. The reaction may be conducted by reacting any amount of tertiary amino groups to epoxy groups sufficient to provide a quaternary ammonium compound. In one embodiment a mole ratio of tertiary amino groups to epoxy groups may range from about 2:1 to about 1:2. When the amine component has an acid number ranging from about 1 to about 200 mgKOH/g, the reaction medium may include from about 0.5 moles to about 2.0 moles of carboxylic acid per mole equivalent of epoxide. When the reaction is completed volatiles and unreacted reagents may be removed from the reaction product by heating the reaction product under vacuum. The product may be diluted with mineral oil, diesel fuel, kerosene, or an inert hydrocarbon solvent to prevent the product from being too viscous, if necessary.

One or more additional optional compounds may be present in the fuel compositions of the disclosed embodiments. For example, the fuels may contain conventional quantities of cetane improvers, corrosion inhibitors, cold flow improvers (CFPP additive), pour point depressants, solvents, demulsifiers, lubricity additives, friction modifiers, amine stabilizers, combustion improvers, dispersants, antioxidants, heat stabilizers, conductivity improvers, metal deactivators, marker dyes, organic nitrate ignition accelerators, cyclomatic manganese tricarbonyl compounds, and the like. In some aspects, the compositions described herein may contain about 10 weight percent or less, or in other aspects, about 5 weight percent or less, based on the total weight of the additive concentrate, of one or more of the above additives. Similarly, the fuels may contain suitable amounts of conventional fuel blending components such as methanol, ethanol, dialkyl ethers, 2-ethylhexanol, and the like.

In some aspects of the disclosed embodiments, organic nitrate ignition accelerators that include aliphatic or cycloaliphatic nitrates in which the aliphatic or cycloaliphatic group is saturated, and that contain up to about 12 carbons may be used. Examples of organic nitrate ignition accelerators that may be used are methyl nitrate, ethyl nitrate, propyl nitrate, isopropyl nitrate, allyl nitrate, butyl nitrate, isobutyl nitrate, sec-butyl nitrate, tert-butyl nitrate, amyl nitrate, isoamyl nitrate, 2-amyl nitrate, 3-amyl nitrate, hexyl nitrate, heptyl nitrate, 2-heptyl nitrate, octyl nitrate, isooctyl nitrate, 2-ethylhexyl nitrate, nonyl nitrate, decyl nitrate, undecyl nitrate, dodecyl nitrate, cyclopentyl nitrate, cyclohexyl nitrate, methylcyclohexyl nitrate, cyclododecyl nitrate, 2-ethoxyethyl nitrate, 2-(2-ethoxyethoxy)ethyl nitrate, tetrahydrofuranyl nitrate, and the like. Mixtures of such materials may also be used.

Examples of suitable optional metal deactivators useful in the compositions of the present application are disclosed in U.S. Pat. No. 4,482,357 issued Nov. 13, 1984, the disclosure of which is herein incorporated by reference in its entirety. Such metal deactivators include, for example, salicylidene-o-aminophenol, disalicylidene ethylenediamine, disalicylidene propylenediamine, and N,N'-disalicylidene-1,2-diaminopropane.

When formulating the fuel compositions of this application, the additives may be employed in amounts sufficient to reduce or inhibit deposit formation in a fuel system or combustion chamber of an engine and/or crankcase. In some aspects, the fuels may contain minor amounts of the above described reaction product that controls or reduces the formation of engine deposits, for example injector deposits in diesel engines. For example, the diesel fuels of this disclosure may contain, on an active ingredient basis, an amount of the quaternary ammonium salt in the range of about 1 mg to about 100 mg of quaternary ammonium salt per Kg of fuel, such as in the range of about 5 mg to about 50 mg of per Kg of fuel or in the range of from about 5 mg to about 25 mg of the quaternary ammonium salt per Kg of fuel. The active ingredient basis excludes the weight of (i) unreacted components associated with and remaining in the product as produced and used, and (ii) solvent(s), if any, used in the manufacture of the product either during or after its formation.

The additives of the present application, including the quaternary ammonium salt described above, and optional additives used in formulating the fuels of this invention may be blended into the base diesel fuel individually or in various sub-combinations. In some embodiments, the additive components of the present application may be blended into the diesel fuel concurrently using an additive concentrate, as this takes advantage of the mutual compatibility and convenience afforded by the combination of ingredients when in the form of an additive concentrate. Also, use of a concentrate may reduce blending time and lessen the possibility of blending errors.

The fuels of the present application may be applicable to the operation of diesel engine. The engine include both stationary engines (e.g., engines used in electrical power generation installations, in pumping stations, etc.) and ambulatory engines (e.g., engines used as prime movers in automobiles, trucks, road-grading equipment, military vehicles, etc.). For example, the fuels may include any and all middle distillate fuels, diesel fuels, biorenewable fuels, biodiesel fuel, fatty acid alkyl ester, gas-to-liquid (GTL) fuels, jet fuel, alcohols, ethers, kerosene, low sulfur fuels, synthetic fuels, such as Fischer-Tropsch fuels, liquid petroleum gas, bunker oils, coal to liquid (CTL) fuels, biomass to liquid (BTL) fuels, high asphaltene fuels, fuels derived from coal (natural, cleaned, and petcoke), genetically engineered biofuels and crops and extracts therefrom, and natural gas. "Biorenewable fuels" as used herein is understood to mean any fuel which is derived from resources other than petroleum. Such resources include, but are not limited to, corn, maize, soybeans and other crops; grasses, such as switchgrass, miscanthus, and hybrid grasses; algae, seaweed, vegetable oils; natural fats; and mixtures thereof. In an aspect, the biorenewable fuel can comprise monohydroxy alcohols, such as those comprising from 1 to about 5 carbon atoms. Non-limiting examples of suitable monohydroxy alcohols include methanol, ethanol, propanol, n-butanol, isobutanol, t-butyl alcohol, amyl alcohol, and isoamyl alcohol.

Accordingly, aspects of the present application are directed to methods for reducing the amount of injector deposits of engines having at least one combustion chamber and one or more direct fuel injectors in fluid connection with the combustion chamber. In another aspect, the quaternary ammonium salts described herein or fuel containing the quaternary ammonium salt may be combined with polyhydrocarbyl-succinimides, -Mannich compounds, -acids, -amides, -esters, -amide/acids and -acid/esters.

In some aspects, the methods comprise injecting a hydrocarbon-based compression ignition fuel comprising a quaternary ammonium salt of the present disclosure through the injectors of the diesel engine into the combustion chamber, and igniting the compression ignition fuel. In some aspects, the method may also comprise mixing into the diesel fuel at least one of the optional additional ingredients described above.

In one embodiment, the diesel fuels of the present application may be essentially free, such as devoid, of polyhydrocarbyl-succinimides, -Mannich compounds, -acids, -amides, -esters, -amide/acids and -acid/esters. In another embodiment, the fuel is essentially free of a quaternary ammonium salt of a hydrocarbyl succinimide or quaternary ammonium salt of a hydrocarbyl Mannich compound. The term "essentially free" is defined for purposes of this application to be concentrations having substantially no measurable effect on injector cleanliness or deposit formation.

EXAMPLES

The following examples are illustrative of exemplary embodiments of the disclosure. In these examples as well as elsewhere in this application, all parts and percentages are by weight unless otherwise indicated. It is intended that these examples are being presented for the purpose of illustration only and are not intended to limit the scope of the invention disclosed herein.

Comparative Example 1

A commercial additive believed to be an alkoxylated quaternary ammonium salt made from a polyisobutylsuccinimide (PIBSI) which is prepared by reacting polyisobutylene succinic anhydride (PIBSA) and dimethylaminopropyl amine (DMAPA) according to U.S. Pat. No. 8,147,569.

Comparative Example 2

A quaternary ammonium salt was prepared by a method according to U.S. Pat. No. 8,147,569. A PIBSI (comparative example 1, about 210 g) was reacted with 1,2-epoxyhexane (36.9 g), acetic acid, (18.5 g) and 2-ethylhexanol (82 g) at a temperature of up to 90° C. for 3 hours. Volatiles were removed under reduced pressure to give the desired quaternary ammonium salt.

Inventive Example 1

A mixture of oleylamido propyl dimethylamine (150 g), 1,2-epoxy butane (59 g), acetic acid (37 g), and methanol (50 g) was heated slowly to 70° C. under an inert atmosphere. The mixture was gently refluxed at 70° C. for 2.5 hour. Volatiles were removed under reduced pressure to give the desired product as a brownish oil having a chlorine content that is undetectable.

Inventive Example 2

A mixture of oleylamido propyl dimethylamine (232 g), 1,2-epoxy butane (91 g), 2-ethylhexanoic acid (136 g), and methanol (93 g) was heated slowly to 70° C. under inert atmosphere. The mixture was gently refluxed at 70° C. for 1 hour, then 75° C. for 2 hours. Volatiles were removed under reduced pressure to give the desired product as a brownish oil.

Inventive Example 3

A quaternary ammonium salt was prepared similarly to that of Inventive Example 1 except that propylene oxide was used in place of 1,2-epoxy butane, and oleic acid was used in place of acetic acid. The reaction was carried out at about 50° C. in a pressured vessel. The resulting product was a brownish viscose oil.

Inventive Example 4

A quaternary ammonium salt was prepared similarly to that of Inventive Example 3 except that polyisobutylene succinic mono methyl ester acid was used in place of oleic acid to give product as a very viscose oil.

Inventive Example 5

A quaternary ammonium salt was prepared similarly to that of Inventive Example 3 except that ethylene oxide was used in place of propylene oxide.

Inventive Example 6

A quaternary ammonium salt was prepared similarly to that of Inventive Example 3, except that dodecyl phenol was used in place of oleic acid and 1,2-butylene oxide was used in place of propylene oxide. The resulting product was a brownish oil.

Inventive Example 7

A quaternary ammonium salt was prepared similarly to that of Inventive Example 6, except that dodecyl phenol was replaced with 3,5-di-tert-butyl-4-hydroxyhydrocinnamic acid $C_{7-9}$ branched alkyl ester. The resulting product was a brownish oil.

Inventive Example 8

A quaternary ammonium salt was prepared similarly to that of Inventive Example 4 except that (1) acetylamido propyldimethyl amine was used in place of oleylamido propyldimethylamine and (2) 1,2-butylene oxide was used in place of propylene oxide to give a product as a very viscose oil.

In the following example, an injector deposit test was performed on a diesel engine using an industry standard diesel engine fuel injector test, CEC F-98-08 (DW10) as described below.

Diesel Engine Test protocol

A DW10 test that was developed by Coordinating European Council (CEC) was used to demonstrate the propensity of fuels to provoke fuel injector fouling and was also used to demonstrate the ability of certain fuel additives to prevent or control these deposits. Additive evaluations used the protocol of CEC F-98-08 for direct injection, common rail diesel engine nozzle coking tests. An engine dynamometer test stand was used for the installation of the Peugeot DW10 diesel engine for running the injector coking tests. The engine was a 2.0 liter engine having four cylinders. Each combustion chamber had four valves and the fuel injectors were DI piezo injectors have a Euro V classification.

The core protocol procedure consisted of running the engine through a cycle for 8-hours and allowing the engine to soak (engine off) for a prescribed amount of time. The foregoing sequence was repeated four times. At the end of each hour, a power measurement was taken of the engine while the engine was operating at rated conditions. The injector fouling propensity of the fuel was characterized by a difference in observed rated power between the beginning and the end of the test cycle.

Test preparation involved flushing the previous test's fuel from the engine prior to removing the injectors. The test injectors were inspected, cleaned, and reinstalled in the engine. If new injectors were selected, the new injectors were put through a 16-hour break-in cycle. Next, the engine was started using the desired test cycle program. Once the engine was warmed up, power was measured at 4000 RPM and full load to check for full power restoration after cleaning the injectors. If the power measurements were within specification, the test cycle was initiated. The following Table 1 provides a representation of the DW10 coking cycle that was used to evaluate the fuel additives according to the disclosure.

TABLE 1

One hour representation of DW10 coking cycle.

| Step | Duration (minutes) | Engine speed (rpm) | Load (%) | Torque (Nm) | Boost air after Intercooler (° C.) |
|---|---|---|---|---|---|
| 1 | 2 | 1750 | 20 | 62 | 45 |
| 2 | 7 | 3000 | 60 | 173 | 50 |
| 3 | 2 | 1750 | 20 | 62 | 45 |
| 4 | 7 | 3500 | 80 | 212 | 50 |
| 5 | 2 | 1750 | 20 | 62 | 45 |
| 6 | 10 | 4000 | 100 | * | 50 |
| 7 | 2 | 1250 | 10 | 25 | 43 |
| 8 | 7 | 3000 | 100 | * | 50 |
| 9 | 2 | 1250 | 10 | 25 | 43 |
| 10 | 10 | 2000 | 100 | * | 50 |
| 11 | 2 | 1250 | 10 | 25 | 43 |
| 12 | 7 | 4000 | 100 | * | 50 |

Various fuel additives were tested using the foregoing engine test procedure in an ultra low sulfur diesel fuel containing zinc neodecanoate, 2-ethylhexyl nitrate, and a fatty acid ester friction modifier (base fuel). A "dirty-up" phase consisting of base fuel only with no additive was initiated, followed by a "clean-up" phase consisting of base fuel with additive. All runs were made with 8 hour dirty-up and 8 hour clean-up unless indicated otherwise. The percent power recovery was calculated using the power measurement at end of the "dirty-up" phase and the power measurement at end of the "clean-up" phase. The percent power recovery was determined by the following formula Percent Power recovery=(DU-CU)/DU×100 wherein DU is a percent power loss at the end of a dirty-up phase without the additive, CU is the percent power at the end of a clean-up phase with the fuel additive, and power is measured according to CEC F98-08 DW10 test.

TABLE 2

| Run | Additives and treat rate (ppm by weight) | Power loss % DU | CU | Power recovery % (DU − CU)/ DU × 100 | Additive Efficiency Power Recovery %/ppm |
|---|---|---|---|---|---|
| 1 | Comparative Example 1 - PIBSI derived quaternary ammonium salt (75 ppm) | −5.2 | −1.43 | 73 | 0.97 |
| 2 | Compound of Comparative Example 2 (150 ppm) | −4.72 | 3.36 | 171 | 1.14 |
| 3 | Compound of Inventive Example 1 (25 ppm) | −2.34 | −0.42 | 82 | 3.28 |
| 4 | Compound of Inventive Example 2 (25 ppm) | −3.9 | 1.86 | 148 | 5.92 |
| 5 | Compound of Inventive Example 3 (25 ppm) | −4.86 | 0.36 | 107 | 4.28 |
| 6 | Compound of Inventive Example 4 (50 ppm) | −4.85 | −0.53 | 89 | 1.78 |
| 7 | Compound of Inventive Example 4 (100 ppm) | −2.68 | 1.44 | 154 | 1.54 |

TABLE 2-continued

| Run | Additives and treat rate (ppm by weight) | Power loss % DU | CU | Power recovery % (DU − CU)/ DU × 100 | Additive Efficiency Power Recovery %/ppm |
|---|---|---|---|---|---|
| 8 | Compound of Inventive Example 5 (30 ppm) | −5.77 | 2.23 | 139 | 4.63 |
| 9 | Compound of Inventive Example 6 (100 ppm) | −3.44 | 1.95 | 157 | 1.57 |

In Table 2, the "Additive Efficiency" is the percent recovery for each part per million of additive in the fuel. As shown by comparing the inventive examples of Runs 3-9 to the comparative examples 1-2, the inventive examples have an unexpectedly much greater efficiency in restoring power than the comparative examples. In other words, the much less of the inventive example is needed to restore power to the same degree as the comparative examples. Additionally, greater power recovery may be obtained with the inventive examples when used in comparable amounts to the comparative examples.

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A fuel soluble additive for a fuel injected diesel engine comprising a quaternary ammonium salt derived from a reaction of an amido amine of the formula

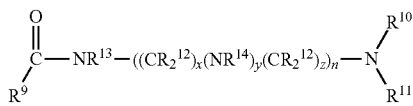

and an epoxide in the presence of a proton donor, wherein $R^9$ is a hydrocarbyl group containing from 2 to 18 carbon atoms, $R^{10}$ and $R^{11}$ are each selected from a hydrocarbyl group containing from 1 to 2 carbon atoms, each $R^{12}$, $R^{13}$ and $R^{14}$ may be independently selected from hydrogen or a hydrocarbyl group, x may range from 1 to 6, y may be 0 or 1, z may be 1 to 6, and n may range from 1 to 6.

2. The fuel additive of claim 1, wherein the proton donor is selected from the group consisting of a carboxylic acid and an alkyl phenol.

3. The fuel additive of claim 1, wherein the epoxide is selected from the group consisting of a hydrocarbyl epoxide of the formula

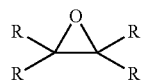

wherein each R is independently selected from H and a $C_1$ to $C_{50}$ hydrocarbyl group, and polyepoxides.

4. The fuel additive of claim 3, wherein the hydrocarbyl epoxide is selected from the group consisting of styrene oxide, ethylene oxide, propylene oxide, butylenes oxide, 1,2-epoxycyclohexane, 2,3-epoxy-5-methylhexane, stilbene oxide, and $C_5$ to $C_{200}$ epoxides.

5. The fuel additive of claim 2, wherein the proton donor is a carboxylic acid selected from the group consisting of fatty acids, formic acid, acetic acid, propionic acid, butyric acid, polyisobutenyl succinic acid, amide/acid, or acid/ester, and polymeric acids, and mixtures thereof.

6. A diesel fuel composition comprising from about 1 to about 100 ppm of the fuel additive of claim 1 based on a total weight of the fuel composition.

7. A diesel fuel composition comprising from about 10 to about 50 ppm of the fuel additive of claim 1 based on a total weight of the fuel composition.

8. A method of improving the injector performance of a direct fuel injected diesel engine comprising operating the engine on a fuel composition comprising a major amount of diesel fuel and from about 5 to about 100 ppm by weight based on a total weight of the fuel composition of a quaternary ammonium salt derived from an amido amine of the formula

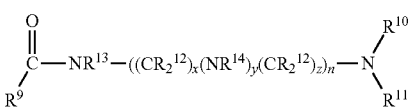

and an epoxide, in the presence of a proton donor selected from the group consisting of a carboxylic acid and an alkyl phenol, wherein $R^9$ is a hydrocarbyl group containing from 2 to 18 carbon atoms, $R^{10}$ and $R^{11}$ are each selected from a hydrocarbyl group containing from 1 to 2 carbon atoms, each $R^{12}$, $R^{13}$ and $R^{14}$ may be independently selected from hydrogen or a hydrocarbyl group, x may range from 1 to 6, y may be 0 or 1, z may be 1 to 6, and n may range from 1 to 6.

9. The method of claim 8, wherein the engine comprises a direct injected diesel engine.

10. The method of claim 8, wherein the epoxide is selected from the group consisting of a hydrocarbyl epoxide of the formula

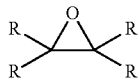

wherein each R is independently selected from H and a $C_1$ to $C_{50}$ hydrocarbyl group, and polyepoxides.

11. The method of claim 8, wherein the proton donor is a carboxylic acid selected from the group consisting of fatty acids, formic acid, acetic acid, propionic acid, butyric acid, polyisobutenyl succinic acid, amide/acid, or acid/ester, and polymeric acids, and mixtures thereof.

12. The method of claim 8, wherein the fuel composition contains from about 10 to about 50 ppm of the quaternary ammonium salt based on a total weight of the fuel composition.

13. A method of operating a fuel injected gasoline engine comprising combusting in the engine a fuel composition comprising a major amount of fuel and from about 5 to about 100 ppm by weight based on a total weight of the fuel composition of a quaternary ammonium salt derived from an amido amine of the formula

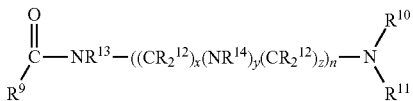

and an epoxide, in the presence of a proton donor selected from the group consisting of a carboxylic acid and an alkyl phenol, wherein $R^9$ is a hydrocarbyl group containing from 2 to 18 carbon atoms, $R^{10}$ and $R^{11}$ are each selected from a hydrocarbyl group containing from 1 to 2 carbon atoms, each $R^{12}$, $R^{13}$ and $R^{14}$ may be independently selected from hydrogen or a hydrocarbyl group, x may range from 1 to 6, y may be 0 or 1, z may be 1 to 6, and n may range from 1 to 6.

* * * * *